United States Patent
Mintie et al.

(10) Patent No.: US 10,561,750 B2
(45) Date of Patent: Feb. 18, 2020

(54) UV DISINFECTING UNIT

(71) Applicant: Mintie Technologies, Inc., Los Angeles, CA (US)

(72) Inventors: James M. Mintie, Long Beach, CA (US); Jose Guadalupe Munoz, Valinda, CA (US); Christopher Foltz, Simi Valley, CA (US)

(73) Assignee: MINTIE, LLC, Azusa, CA (US)

( * ) Notice: Subject to any disclaimer, the term of this patent is extended or adjusted under 35 U.S.C. 154(b) by 0 days.

(21) Appl. No.: 15/623,340

(22) Filed: Jun. 14, 2017

(65) Prior Publication Data

US 2017/0368213 A1   Dec. 28, 2017

Related U.S. Application Data

(60) Provisional application No. 62/355,457, filed on Jun. 28, 2016.

(51) Int. Cl.
  *A61L 2/10* (2006.01)
  *A61L 2/26* (2006.01)

(52) U.S. Cl.
  CPC .................... *A61L 2/10* (2013.01); *A61L 2/26* (2013.01); *A61L 2202/11* (2013.01); *A61L 2202/122* (2013.01); *A61L 2202/16* (2013.01); *A61L 2202/24* (2013.01)

(58) Field of Classification Search
  CPC .......... A61L 2/10; A61L 2/26; A61L 2202/11; A61L 2202/122; A61L 2202/16; A61L 2202/24
  See application file for complete search history.

(56) References Cited

U.S. PATENT DOCUMENTS

| | | | |
|---|---|---|---|
| D197,873 S | 3/1964 | Few et al. | |
| 5,134,025 A * | 7/1992 | Zenda | ................. D06N 3/0043 428/317.9 |
| D404,828 S | 1/1999 | Matsunaga et al. | |
| D433,147 S | 10/2000 | Florkey et al. | |
| 7,875,247 B2 * | 1/2011 | Clark | ..................... A61L 9/205 250/455.11 |
| D674,504 S | 1/2013 | Schenk | |
| D703,343 S | 4/2014 | Biswas et al. | |
| 9,198,990 B2 * | 12/2015 | Fletcher | .................... A61L 2/10 |
| 9,534,407 B2 | 1/2017 | Ballantyne et al. | |

(Continued)

FOREIGN PATENT DOCUMENTS

| CN | 203232241 U | 10/2013 |
|---|---|---|
| EP | 2537600 A1 | 12/2012 |

(Continued)

OTHER PUBLICATIONS

Invitation to Pay Additional Fees and, Where Applicable, Protest Fee issued in corresponding International Application No. PCT/US2017/037569, Sep. 12, 2017, 14 pages.

(Continued)

*Primary Examiner* — David E Smith
(74) *Attorney, Agent, or Firm* — Lewis Roca Rothgerber Christie LLP

(57) ABSTRACT

A UV disinfection unit includes a frame, a flexible envelope supported by the frame, the envelope having a reflective inner surface defining an inner volume for receiving an object to be disinfected, and a UV source for being received in the volume.

25 Claims, 5 Drawing Sheets

(56) References Cited

U.S. PATENT DOCUMENTS

| | | | |
|---|---|---|---|
| D787,084 S | 5/2017 | Sarchese et al. | |
| D799,713 S | 10/2017 | Murphy et al. | |
| D831,147 S | 10/2018 | Cropley et al. | |
| 2004/0050008 A1* | 3/2004 | Mintie | B08B 15/00 52/646 |
| 2004/0074212 A1* | 4/2004 | Yachi | A61G 10/005 55/385.2 |
| 2004/0166018 A1* | 8/2004 | Clark | A61L 9/205 422/4 |
| 2010/0122783 A1* | 5/2010 | Harris | A47H 23/08 160/405 |
| 2012/0325279 A1 | 12/2012 | Munoz | |
| 2014/0158910 A1* | 6/2014 | Fletcher | A61L 2/10 250/455.11 |
| 2014/0326282 A1 | 11/2014 | Kawachi | |
| 2016/0317686 A1* | 11/2016 | Dayton | A61L 2/10 |
| 2019/0030198 A1 | 1/2019 | Mauzerall et al. | |

FOREIGN PATENT DOCUMENTS

| | | | |
|---|---|---|---|
| EP | 1778055 B1 | 1/2014 | |
| WO | WO 2004/011163 A1 | 2/2004 | |
| WO | WO 2015/054389 A2 | 4/2015 | |
| WO | WO 2016/073463 A1 | 5/2016 | |
| WO | WO 2016073463 A1 * | 5/2016 | A61L 2/10 |

OTHER PUBLICATIONS

International Search Report & Written Opinion issued in corresponding International Application No. PCT/US2017/037569, dated Jan. 31, 2018, 23 pages.

International Preliminary Report on Patentability dated Jan. 1, 2019 for corresponding PCT Application No. PCT/US2017/03756, 11 pages.

International Preliminary Report on Patentability Chapter I conducted by the European Patent Office issued in corresponding PCT Application No. PCT/US2017/037569, dated Jan. 10, 2019, 12 pages.

* cited by examiner

UV DISINFECTING UNIT

CROSS-REFERENCE TO RELATED APPLICATION

The present application claims priority to and the benefit of U.S. Provisional Application No. 62/355,457, filed Jun. 28, 2016, entitled "UV CONTAINMENT UNIT, the entire content of which is incorporated herein by reference.

BACKGROUND

Multiple studies have demonstrated that surfaces in hospital rooms of patients are colonized or infected with healthcare-associated pathogens becoming contaminated. Studies have also confirmed that manual cleaning of these contaminated fomites with chemical disinfectants is not adequate. The Center for Disease Control and Prevention (CDC) estimates that one in 25 hospital patients has a health-care acquired infection (HAI) on any single day in the US., and over 10% are fatal.

Hospitals also face challenges to do an adequate job in disinfecting the multitude of fomites, such as portable medical equipment such as carts, imaging equipment, IV poles etc., used at the hospital, where it may be impractical to deploy the UV device where the equipment is located. In addition the cycle time and energy it currently takes to disinfect a room is always a concern at healthcare facilities.

SUMMARY

An example embodiment UV disinfection unit includes a frame and a flexible envelope supported by the frame. The envelope has an inner surface defining an inner volume for receiving an object to be disinfected. The unit also includes a UV source for being received is the volume. In another example embodiment, the frame and envelope are collapsible. In yet another example embodiment, the inner surface has a reflectivity of at least 50%. In a further example embodiment, the inner surface has a reflectivity of at least 70%. In yet a further example embodiment, the inner surface has a reflectivity of at least 75%. In one example embodiment, the inner surface has a reflectivity of at least 95%. In another example embodiment, the envelope includes a main body portion and an arm portion cantilevered from the main body portion, and the main body portion and arm portion define the inner volume. In yet another example embodiment, the arm portion includes a lower surface having an opening for receiving the UV source. In a further example embodiment, the opening includes at least an extra weight coupled to the envelope proximate its perimeter. In yet a further example embodiment, the UV source includes an annular depression for receiving the extra weight. In one example embodiment, the envelope includes an opening for receiving the object to be disinfected there-through.

In another example embodiment, a UV containment envelope is flexible and collapsible and has an inner surface defining an inner volume for receiving an object to be disinfected. The inner surface has a reflectivity of at least 50%. In a further example embodiment, the inner surface has a reflectivity of at least 70%. In yet a further example embodiment, the inner surface has a reflectivity of at least 75%. In one example embodiment, the inner surface has a reflectivity of at least 95%. In another example embodiment, the envelope includes a main body portion and an arm portion cantilevered from the main body portion, and the main body portion and arm portion define the inner volume.

In yet another example embodiment, the arm portion includes a lower surface having an opening for receiving a UV source. In a further example embodiment, the opening includes at least an extra weight coupled to the envelope proximate its perimeter. In one example embodiment, the envelope includes an opening for receiving the object to be disinfected there-through.

DETAILED DESCRIPTION

Figure 1:
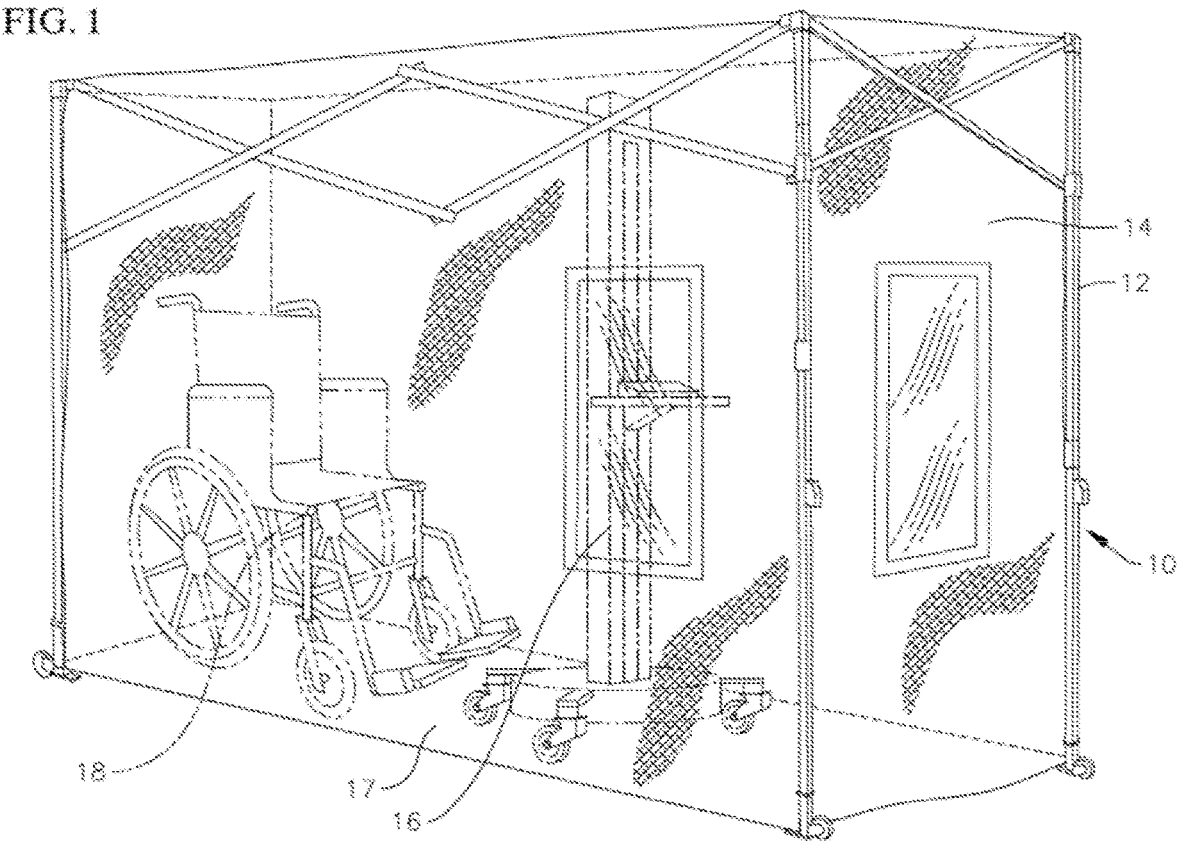
FIG. 1 is perspective see-through views of the example embodiment UVDU.

An example embodiment UV Disinfecting Unit (UVDU) 10 is shown in FIG. 1. The example embodiment UVDU includes a frame 12, which is a collapsible frame 12 which supports an envelope 14. In the shown example embodiments, the envelope is supported by the frame within the frame. Example embodiment frames and envelop designs as well as the coupling of such envelopes to the frames are disclosed in U.S. Pat. Nos. 7,134,444 and 7,406,978, as well as U.S. Patent Publication No. 2012/0325,279, all three of which are fully incorporated into this application by reference ("the incorporated patents"). The size of the frame may vary. The size of the envelope may vary. In an example embodiment, the thickness of the envelope may be 3 mils or less. In the further example embodiment, the envelope may be disposable. The envelope may have multiple openings that may close with various known methods, as for example described in the incorporated patents to receive a UV device 16, as for example an ultraviolet C (UVC) light lamp that emits a UV light capable of disinfecting and/or sanitizing fomites. UVC has a wave length in the range of 100 nm to 290 nm. The size of the UV device or lamp may vary for the size of the envelope.

The envelope may be sized to be able to receive all types fomites 18 including incubators, wheelchairs, poles, and medical devices that are used to monitor patients in hospitals, as well as chairs and other furniture that may be used in hospital rooms. To do so, the envelope is equipped with the appropriate size opening(s). The opening may be closed with a door that attaches to the perimeter of the opening. For example, the door opening can be a separate panel made from the same material as the envelope and attaches to the perimeter of the opening as for example with a zipper or Velcro or other well-known fasteners. In other example embodiments, the door is a flap formed on the envelope which when folded away reveals the opening and which attaches at least an end of the opening using fasteners such as for example zippers or Velcro. For example, a front panel 17 of the envelope 14 may be a flap that folds away that allows for larger objects to be inserted into the envelope for disinfection. In other example embodiments, the opening is a slit that is formed on the envelope that may be closed using fasteners such as for example zippers or Velcro.

Once the fomites and the UV device are within the envelope, the envelope is closed and the UV device is turned on for the appropriate amount of time to disinfect and/or sterilize the equipment inserted into the UVDU through an opening and the opening is closed.

Example embodiment envelopes are also flame resistant. An example embodiment envelope is flame-rated to U.S. NFPA 701 standards. In example embodiment, the envelope has a weight of about 28 lbs, a footprint of about 35 by 86 inches and a height of about 88 inches. The envelope has a door to accept fomites being in an example embodiment about 48 by 102 inches in dimension.

In an example embodiment, the envelope has its inner surface either coated or covered with a material, or the entire envelope is made from a material, that has a desired reflectivity. A desired reflectivity in the example embodiment is 50% or greater. In an example embodiment, the reflectivity is 70% or greater. In one example embodiment the reflectivity is 73%. In another example embodiment, the reflectivity is 75%. In an example embodiment, the reflectivity is 95% or greater. In yet another example embodiment, the reflectivity is 99%, In a further example embodiment, the reflectivity is greater than 99%. Reflectivity may be measured with well-known methods and devices, such as a spectral reflectometer. When the UV device is placed in an enclosed space, the UV light reached only those surfaces which are direct line of slight of the light. However, surfaces or areas which are shadowed or not in line of sight do not get the benefits of UV irradiation. By having the envelope walls formed from a fabric with the desired reflectivity or having the inner surfaces of the envelope covered with a reflective coating, the UV light form the UV source is reflected to these shadowed areas via specular or diffuse reflection. UV reflective materials which may be used to form or coat the fabric forming the envelope include ePTFE, aluminum and magnesium. Magnesium has a reflectivity of at least 75%. Aluminum has a reflectivity of at least 73%. ePTFE made by W.L. Gore has a reflectivity of at least 95%.

Figure 2:
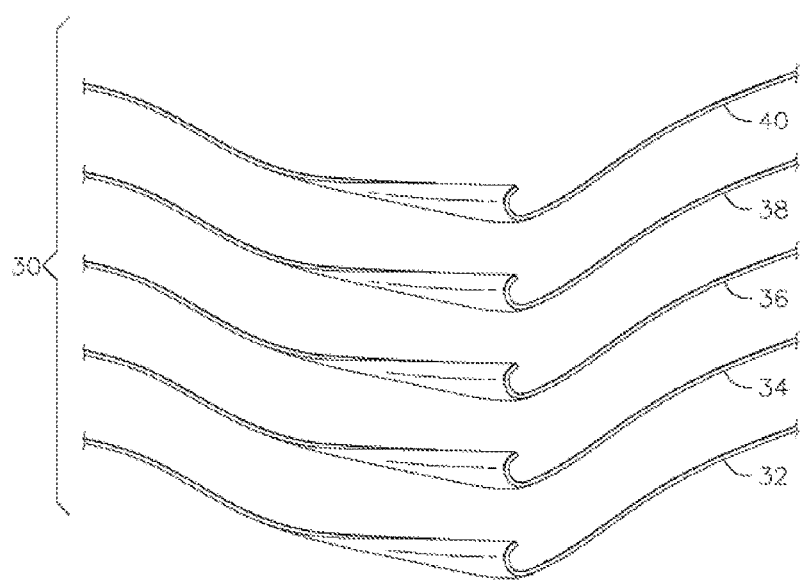
FIG. 2 is blow-up view of an example embodiment material used to form an example embodiment envelope.

To obtain the appropriate reflectivity, in an example embodiment, the material forming the envelope is aluminized. An example aluminized material 30 includes an outer fabric layer 32, a heat stable adhesive 34 adhering the fabric layer 32 to a first aluminum layer 36, as shown in FIG. 2. A protective film 38 is formed over the first aluminum layer 36 and a second, or inner, aluminum layer 38 if formed over the protective layer. Fabric layer 32 defines the outer surface of the envelope whereas inner aluminum layer 38 defines the reflective inner surface of the envelop. In an example, embodiment an appropriate aluminized fabric may be obtained from Gentex Corporation. In another example embodiment, as appropriate fabric forming the outer layer 32 is forwarded to Gentex Corporation for aluminizing. An example fabric layer 32 has a yarn size of 150 Dernier, a thread count in ends per square inch of 84T, a thread count in fillings per square inch of 48T, a yarn weight of 130 g/sqm, and a thickness of about 0.28 mm. When coated with a coating (e.g., layers 34, 36, 38 and 40), the coating has a weight of 35 g/sqm and a thickness of about 0.025 mm.

Figure 3:
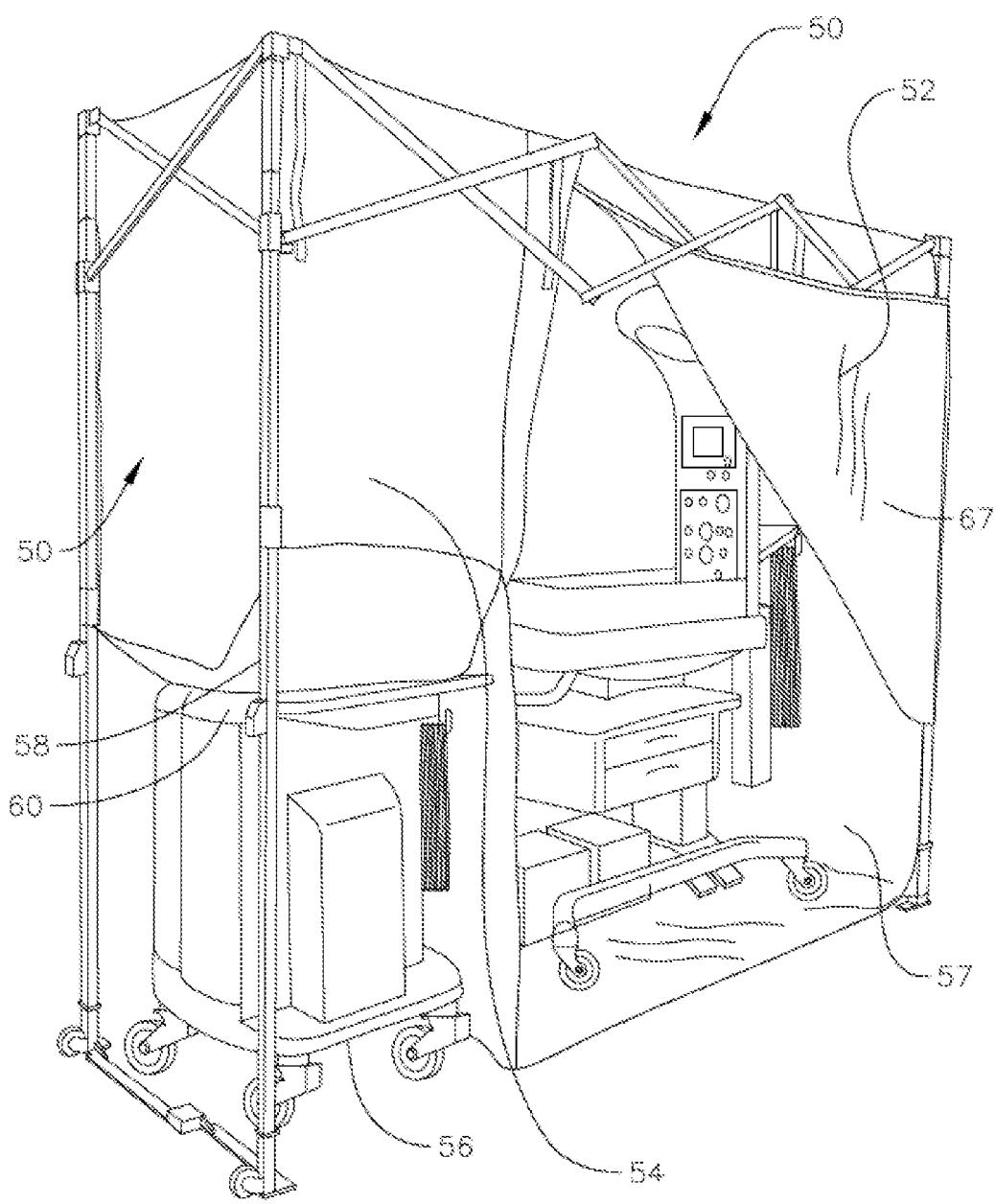
FIG. 3 is a perspective view of another example embodiment UVDU.
Figure 5:
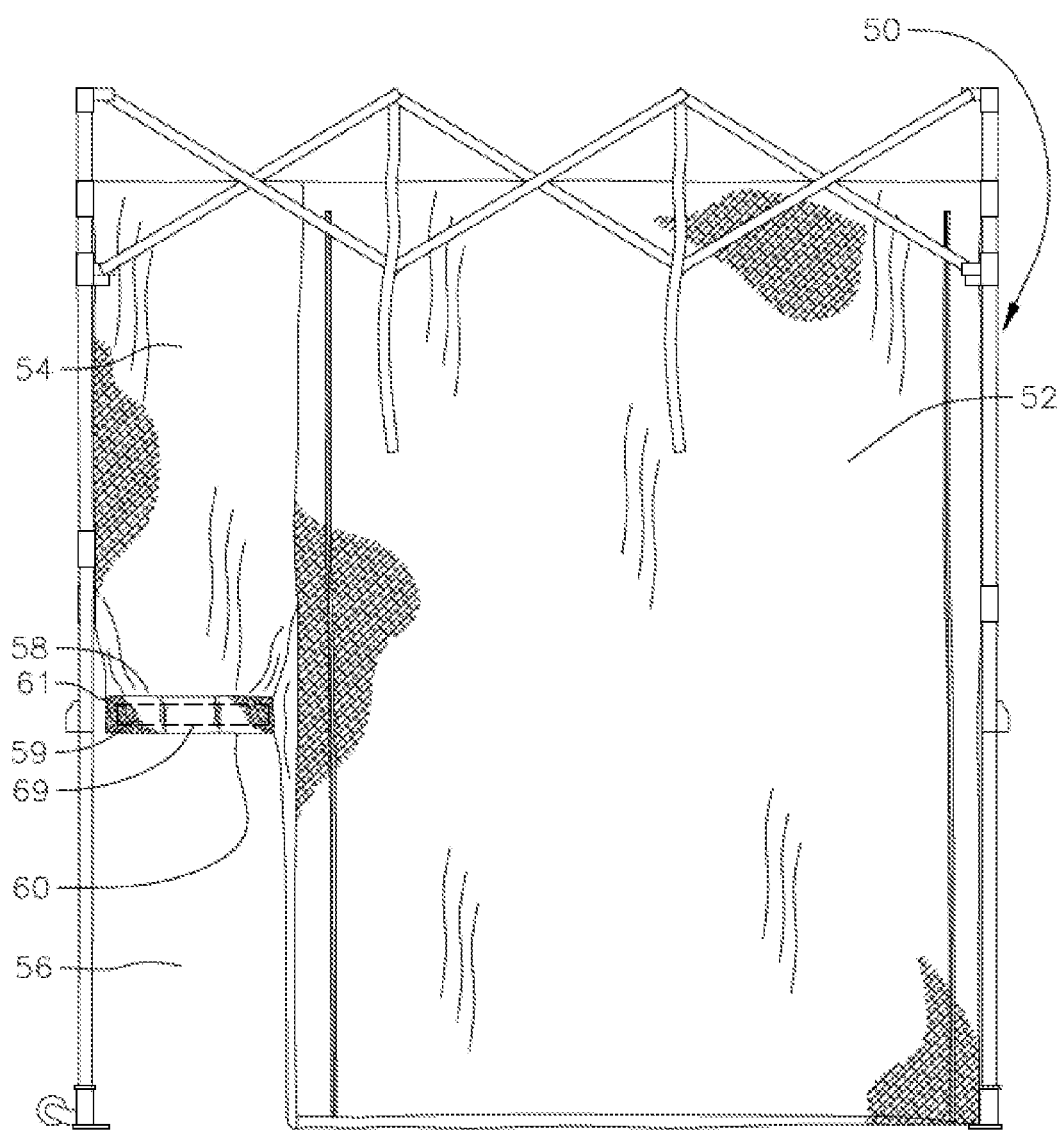
FIG. 5 is a front view of the example embodiment UVDU shown if FIG. 3 without the UV source.
Figure 6:
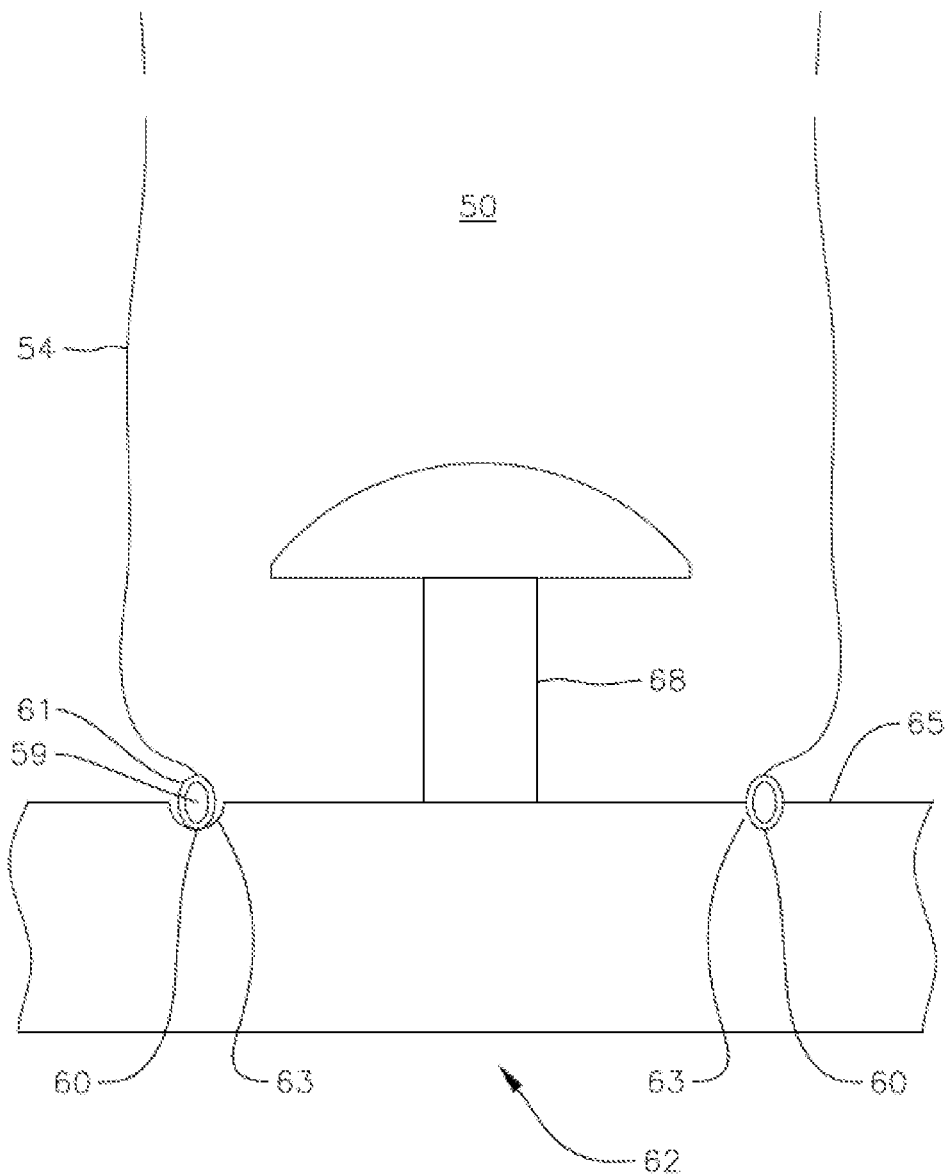
FIG. 6 is a partial cross-sectional view of the arm portion of the example embodiment UVDU shown in FIG. 3 mated with a UV source.

In an example embodiment, an envelope 50 is used that has an upside down L shape as for example shown in FIGS. 3, 5 and 6. In other words, the envelope has a main portion 52, as for example a rectangular of square portion in plan view, from which extends (e.g. is cantilevered) an arm portion 54, which in an example embodiment may be square or rectangular in plan view, such that an empty space 56 is defined below the arm portion. In the shown example embodiment, both the main portion and the arm portion are cubic. The empty space allows a UV light source to be placed therein. In an example embodiment, at a bottom surface 58 of the arm portion is formed an opening 60 to receive a UV light source. An opening 57 sealable or closeable by a flap 67 provides access to the envelope interior for placing the objects to be disinfected therein. The opening in the shown example embodiment is formed on a front face of the main portion 52 of the envelope.

Figure 4:
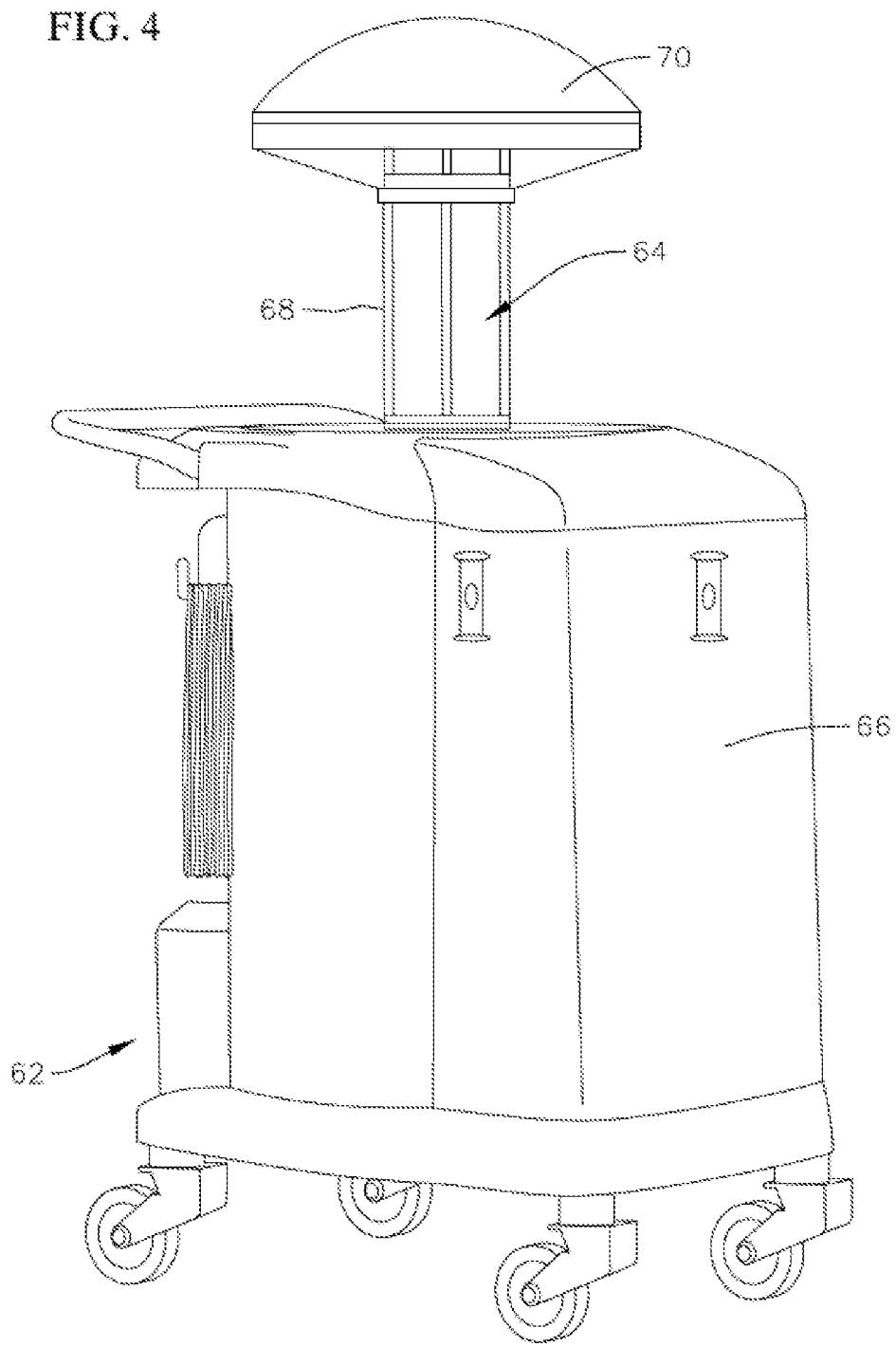
FIG. 4 is a perspective view of an example embodiment UV source.

In an example embodiment, the UV light source is a device produced by Xenex Disinfection Services, LLC and marketed under the name Lightstrike Disinfection Robot (herein the "robot"). LIGHTSTRIKE is a trademark of Xenex Disinfection Services, LLC. The robot 62, as shown in FIG. 4 has a UV emitting source 64, for emitting UVC light, that extends from a body 66 of the robot. The source retracts into the body when not in use. In an example embodiment, the UV emitting source includes a neck 68 and a head 70 extending from the neck. In the example embodiment shown in FIG. 4, the robot is received in the space 56 below the arm portion 54 of the envelope. The height of the space is such when the robot is placed in the space, the lower surface 58 of the arm portion of the envelope rests against an upper surface 65 the robot body 66. In this regard the neck and head are extended through the lower surface opening 60 and into the envelope 50. To ensure that the lower surface 58 of the arm portions contacts the robot body, and ring 59 is adhered or otherwise coupled at the perimeter or proximate the perimeter of the opening 60 so that it surrounds the opening 60 as for example shown in FIGS. 5 and 6. The ring may be made from any type material that provides sufficient weight for causing the perimeter of the opening 60 or the envelope portion surrounding the perimeter opening to move toward and rest on the body of the robot. For example the ring may be a thick wire that is placed in a pocket 61 surrounding the opening. The ring may be a one solid ring or may be formed in parts. In other example embodiments, spaced apart weights may be placed surrounding the opening. To ensure a better contact or even a seal between the lower surface and the body of the robot, an annular depression 63 may be formed on the robot 62 surrounding the neck 68 to receive the ring or the weight(s) surrounding the opening, as for example shown in FIG. 6. The opening has a diameter 60 sufficient to allow for penetration by the head. In an example embodiment the opening has a diameter just slightly larger than the diameter of the head.

In an example embodiment, the UVDU is portable and collapsible and is deployed within minutes in any area of the healthcare facility. A portable UV device 16 may be wheeled into the containment unit with various fomites. The UV device in the device may be turned on and off remotely. After the disinfection or sterilization process is accomplished the fomites 18 and UV device 16 are removed from the UVDU.

The example embodiment UVDU is highly advantageous in being able to isolate and enclose various fomites in an easy to install, minimal set up time, easy to store, collapsible and portable, easy to clean, flame-resistant/durable envelope with a sealed enclosure and thereby quickly disinfecting them with the portable UV device. The example embodiment UVDU reduces cycle time and increases the "kill rate."

Example embodiment UVDUs are highly advantageous to be able to isolate and enclose various fomites. Example embodiment UVDUs are easy to install, easy to store, collapsible and portable, easy to clean, and have a flame-resistant durable envelope sealed enclosure.

Testing with the example embodiment envelopes and example embodiment UV sources saw over 99%, as for example over 99.9%, elimination of C diff, MRSA, CRE, VER and other MDROs.

While example embodiment disinfection units have been described with being used with collapsible frame, in other example embodiments any example envelope may be mounted on a fixed frame that is not collapsible and may or may not be portable.

Although a few example embodiments have been described in detail above, those skilled in the art will readily appreciate that many modifications are possible in the example embodiments without materially departing from this invention. The embodiments described herein are not intended to be exhaustive or to limit the scope of the invention to the exact forms disclosed. Accordingly, all such modifications are intended to be included within the scope of this disclosure as defined in the following claims. It is the express intention of the applicant not to invoke 35 U.S.C. 112, paragraph 6 for any limitations of any of the claims herein, except for those in which the claim expressly uses the words 'means for' together with an associated function.

The invention claimed is:

1. A UV disinfection unit comprising:
   a frame;
   a flexible envelope supported by the frame, said envelope having an inner surface formed from a fabric having a reflectivity of at least 50% and defining an inner volume having a first portion for receiving at least a fomite having the size of a wheel chair to be disinfected and a second portion; and
   a UV source for being received in said volume second portion, wherein the second portion is cantilevered from the first position.

2. The unit as recited in claim 1, wherein the frame and envelope are collapsible.

3. The unit as recited in claim 1, wherein said fabric has a reflectivity of at least 70%.

4. The unit as recited in claim 1, wherein said fabric has a reflectivity of at least 75%.

5. The unit as recited in claim 1, wherein said fabric has a reflectivity of at least 95%.

6. The unit as recited in claim 1, wherein the second portion comprises an opening comprising at least an extra weight coupled to the envelope proximate its perimeter.

7. The unit as recited in claim 6, wherein the UV source comprises an annular depression for receiving said extra weight.

8. The unit as recited in claim 1, wherein the envelope comprises an opening for receiving the object to be disinfected there-through.

9. The unit as recited in claim 1, wherein the fabric is an aluminized fabric.

10. A UV containment envelope, said envelope being flexible and collapsible and having an inner surface defining an inner volume comprising a first portion for receiving at least a fomite having the size of a wheel chair to be disinfected, said inner surface formed from a fabric having a reflectivity of at least 50% and a second portion cantilevered from the first portion for receiving a UV source.

11. The envelope as recited in claim 10, wherein said fabric has a reflectivity of at least 70%.

12. The unit as recited in claim 10, wherein said fabric has a reflectivity of at least 75%.

13. The envelope as recited in claim 10, wherein said fabric has a reflectivity of at least 96%.

14. The envelope as recited in claim 10, wherein the second portion comprises an opening comprising at least an extra weight coupled to the envelope proximate its perimeter.

15. The envelope as recited in claim 10, further comprising an opening for receiving said equipment therethrough.

16. The envelope as recited in claim 10, wherein the fabric is an aluminized fabric.

17. A UV disinfection unit comprising:
   a frame;
   a flexible envelope supported by the frame, said envelope having an inner surface formed from a fabric having a reflectivity of at least 50% and defining an inner volume comprising a first portion and a second portion cantilevered from the first portion for receiving an object to be disinfected; and
   a UV source for being received is said second portion, and wherein each of the first and second portion comprise an inner surface formed from a fabric comprising a reflectivity of at least 50%.

18. The unit as recited in claim 17, wherein the second portion comprises an opening comprising at least an extra weight coupled to the envelope proximate its perimeter.

19. The unit as recited in claim 18, wherein the UV source comprises an annular depression for receiving said extra weight.

20. A UV disinfection unit comprising:
   a frame;
   a flexible envelope supported by the frame, said envelope having an inner surface defining an inner volume for receiving an object to be disinfected; and
   a UV source for being received is said volume, wherein the envelope comprises a main body portion and an arm portion cantilevered from the main body portion, wherein the main body portion and arm portion define said inner volume, and wherein the arm portion comprises a lower surface having an opening for receiving the UV source.

21. The unit as recited in claim 20, wherein the opening comprises at least an extra weight coupled to the envelope proximate its perimeter.

22. The unit as recited in claim 21, wherein the UV source comprises an annular depression for receiving said extra weight.

23. The unit as recited in claim 20, wherein the fabric is an aluminized fabric.

24. A UV containment envelope, said envelope being flexible and collapsible and having an inner surface defining an inner volume for receiving an object to be disinfected, said inner surface having a reflectivity of at least 50%, wherein the envelope comprises a main body portion and an arm portion cantilevered from the main body portion, wherein the main portion and arm portion define said inner volume, wherein the arm portion comprises a lower surface having an opening for receiving a UV source.

25. The envelope as recited in claim 24, wherein the opening comprises at least an extra weight coupled to the envelope proximate its perimeter.

* * * * *

UNITED STATES PATENT AND TRADEMARK OFFICE
CERTIFICATE OF CORRECTION

PATENT NO. : 10,561,750 B2  
APPLICATION NO. : 15/623340  
DATED : February 18, 2020  
INVENTOR(S) : James M. Mintie et al.

Page 1 of 1

It is certified that error appears in the above-identified patent and that said Letters Patent is hereby corrected as shown below:

In the Claims  
Column 6, Line 1, Claim 12      delete "unit" and insert -- envelope --

Signed and Sealed this  
Fifteenth Day of December, 2020

Andrei Iancu  
*Director of the United States Patent and Trademark Office*